(12) United States Patent
Wong

(10) Patent No.: US 8,003,944 B2
(45) Date of Patent: Aug. 23, 2011

(54) SATURATION FILTERING NDIR GAS SENSING METHODOLOGY

(75) Inventor: Jacob Y Wong, Goleta, CA (US)

(73) Assignee: Airware, Inc., Goleta, CA (US)

(*) Notice: Subject to any disclaimer, the term of this patent is extended or adjusted under 35 U.S.C. 154(b) by 0 days.

(21) Appl. No.: 12/759,603

(22) Filed: Apr. 13, 2010

(65) Prior Publication Data

US 2010/0258728 A1     Oct. 14, 2010

Related U.S. Application Data

(60) Provisional application No. 61/212,713, filed on Apr. 14, 2009.

(51) Int. Cl.
*G01J 5/58* (2006.01)

(52) U.S. Cl. .................................. 250/339.06

(58) Field of Classification Search ............ 250/339.13, 250/338.1, 339.01, 339.06, 339.12, 340, 250/341.1, 343
See application file for complete search history.

(56) References Cited

U.S. PATENT DOCUMENTS

| | | | | |
|---|---|---|---|---|
| 4,027,972 A | * | 6/1977 | Davies ............................. | 356/51 |
| 4,103,163 A | * | 7/1978 | Hamada ........................ | 250/344 |
| 4,288,693 A | * | 9/1981 | Fabinski et al. ................ | 250/345 |
| 4,332,770 A | * | 6/1982 | Ishida et al. ..................... | 422/78 |
| 5,572,031 A | * | 11/1996 | Cooper et al. ................. | 250/343 |
| 5,747,809 A | * | 5/1998 | Eckstrom ....................... | 250/345 |
| 5,764,354 A | * | 6/1998 | Aidam et al. ............... | 356/243.1 |
| 5,900,635 A | * | 5/1999 | Weckstrom ................... | 250/345 |
| 7,351,954 B2 | * | 4/2008 | Zhang et al. ................ | 250/252.1 |
| 2005/0012042 A1 | * | 1/2005 | Weckstrom et al. .......... | 250/343 |
| 2007/0029487 A1 | * | 2/2007 | Wong et al. .............. | 250/339.13 |
| 2007/0034792 A1 | * | 2/2007 | Zhang et al. ................ | 250/252.1 |
| 2007/0279633 A1 | * | 12/2007 | Yi et al. ........................ | 356/432 |
| 2009/0257064 A1 | * | 10/2009 | Tkachuk ....................... | 356/453 |
| 2010/0078563 A1 | * | 4/2010 | Haveri et al. ............ | 250/339.06 |
| 2011/0042570 A1 | * | 2/2011 | Wong ............................ | 250/340 |
| 2011/0049342 A1 | * | 3/2011 | Tsao et al. ................. | 250/252.1 |

* cited by examiner

*Primary Examiner* — David P Porta
*Assistant Examiner* — David S Baker
(74) *Attorney, Agent, or Firm* — Roy L. Anderson; Wagner, Anderson & Bright, P.C.

(57) ABSTRACT

NDIR gas sensing methodology is advanced which renders the output of an NDIR gas sensor, when implemented with this new methodology, to remain stable or drift-free over time. Furthermore, the output of such a sensor will also be independent of the temperature of an environ wherein the sensor is in physical contact. This method utilizes the same narrow band-pass spectral filter for the detection of the gas of interest for both the signal and the reference channels. By so doing, the two channels always receive radiation of the same spectral content from the infrared source of the sensor convoluted with that from any external elements exposed to the sensor. While the same sample chamber through which the gas of interest to be detected flows is shared by the two channels, the detector package for the reference channel is hermetically sealed with 100% of the gas to be detected instead of 100% $N_2$ as for the signal detector. In so doing, the reference channel is rendered almost completely "blind" to the presence or absence of the gas of interest flowing in the common sample chamber thereby creating an absorption bias or difference between the two channels enabling the concentration of the gas of interest to be detected by ratioing the outputs of the two channels via calibration.

17 Claims, 4 Drawing Sheets

US 8,003,944 B2

SATURATION FILTERING NDIR GAS SENSING METHODOLOGY

CROSS-REFERENCE TO RELATED APPLICATIONS

The present application is a continuation-in-part application of U.S. patent application Ser. No. 61/212,713 filed Apr. 14, 2009 entitled "Saturation filtering NDIR methodology."

FIELD OF THE INVENTION

The present application is in the field of gas analysis, and specifically relates to apparatus using a Non-Dispersive Infrared (NDIR) gas analysis technique to determine the concentration of a particular type of gas present in a sample chamber by sensing the absorption of infrared radiation passing through the gas.

BACKGROUND OF THE INVENTION

The Non-Dispersive Infrared ("NDIR") technique has long been considered as one of the best methods for gas measurement. In addition to being highly specific, NDIR gas analyzers are also very sensitive, stable, reliable and easy to maintain and service. Ever since the NDIR technique of gas measurement was first introduced and practiced in the mid 1950's, a large number of improved measurement techniques based upon the NDIR principle for gas detection have been proposed and successfully demonstrated. The most notable advances over the years in this field are summarized as follows.

Burch et al. (U.S. Pat. No. 3,793,525) and Blau et al. (U.S. Pat. No. 3,811,776) in 1974 were the first to advance a so-called "Double Beam" technique for NDIR gas measurement by taking advantage of the principle of nonlinear absorption for some strongly absorbing gases such as $CO_2$ to create a reference channel. Shortly thereafter, this "Double Beam" NDIR gas sensor technique was greatly simplified with the use of two interposed spectral filters (one absorbing and one neutral) to create a sample and a reference detector channel. Subsequent NDIR gas sensors, designed using this technique, have enjoyed good performance alluded to briefly above.

In U.S. Pat. No. 4,578,762 (1986) Wong advanced the first self-calibrating NDIR $CO_2$ analyzer using a novel two-wheel chopper and mirror arrangement. Another improved type of such gas analyzer is shown and described in U.S. Pat. No. 4,694,173 (1987) by Wong. This gas sensor has no moving parts for effecting the interposition of spectral filters to create both a sample and reference detector channel as in the NDIR gas analyzers described earlier.

In U.S. Pat. No. 5,163,332 (1992), Wong advanced the so-called "wave-guide" sample chamber concept for simplifying NDIR gas sensors into ones that are compact, rugged and low-cost while still maintaining their superior performance characteristics. This concept has subsequently been widely adopted in the design of today's NDIR gas sensors, particularly in low-cost and high volume versions.

All of the NDIR gas analyzers described above for the measurement of the concentrations of one or more gases in a mixture perform well functionally and have contributed successfully to the overall technical advancement in the field of gas analysis during the past two decades. They have been widely accepted in both the medical and industrial communities. Despite their undisputed success over the years, there still remain a number of important sensor performance characteristics that need to be greatly improved in order to further extend the useful applications of these devices in a number of areas.

By far the most deficient performance characteristic of gas sensors of today, inclusive of NDIR gas sensors, is the sensor output stability over time. Unlike the temperature controller or thermostat device which just about everybody is familiar with at home or in their workplaces for sensing temperature and never requires output adjustment or recalibration over time, such is not the case for gas sensors irrespective of their operational principle, functional design, material construct or even costs. Dependent upon the type of gas sensors, just about every one of them requires recalibration once every six months to a year without exception in order that they remain accurate over time. While this performance deficiency has been well tolerated over the years, it remains as a significant drawback for gas sensors and even precludes their use in a number of vital applications and must therefore be eventually eliminated.

The second most prominent performance deficiency for gas sensors of today irrespective of their operational principle is their output dependence as a function of the temperature of the environment wherein the sensors are located. This performance deficiency for just about all gas sensors is universally, albeit reluctantly, dealt with by specifying the output correction per degree of temperature change with respect to the output stipulated at a standard temperature. In some gas sensors these output temperature corrections are quite large and in many cases severely limit the use of these sensors outdoors. It would be a significant step forward in the development of future gas sensors, particularly for the NDIR type, because of its prevalent use in most industries, that this performance deficiency be also overcome.

SUMMARY OF THE INVENTION

The present invention is generally directed to an apparatus and method utilizing a single narrow band-pass spectral filter in a non-dispersive infrared sensor for both a signal channel and a reference channel used to detect a gas of interest wherein the reference channel also contains a saturation cell containing the gas of interest and both a signal detector and a reference detector are mounted on a single thermal platform.

In a first, separate group of aspects of the present invention, the reference channel signal remains substantially unchanged irrespective of the absence or presence of the gas to be detected in any concentration level in a sample chamber of the non-dispersive infrared sensor. The saturation cell can have a length L' and contain a concentration c' of the gas of interest such that a resulting saturation cell concentration of the gas of interest of (L')×(c') is at least an order of magnitude greater than a sample cell concentration of the gas of interest of (L)×(c) where L is a length of the sample cell and c is a maximum concentration of the gas of interest in the sample cell.

In a second, separate group of aspects of the present invention, the reference detector and the signal detector are mounted in a single structure of a heat transmitting material such as aluminum.

In a third, separate group of aspects of the present invention, the chosen absorption band of the gas of interest is a strong absorption band such as, for example, water vapor, a hydrocarbon or carbon dioxide.

It is therefore a primary object of the present invention to advance a new design for NDIR gas sensors and methodology aimed at minimizing drift over time.

This and further objects and advantages will be apparent to those skilled in the art in connection with the drawings and the detailed description of the invention set forth below.

DETAILED DESCRIPTION OF THE INVENTION

Figure 1:
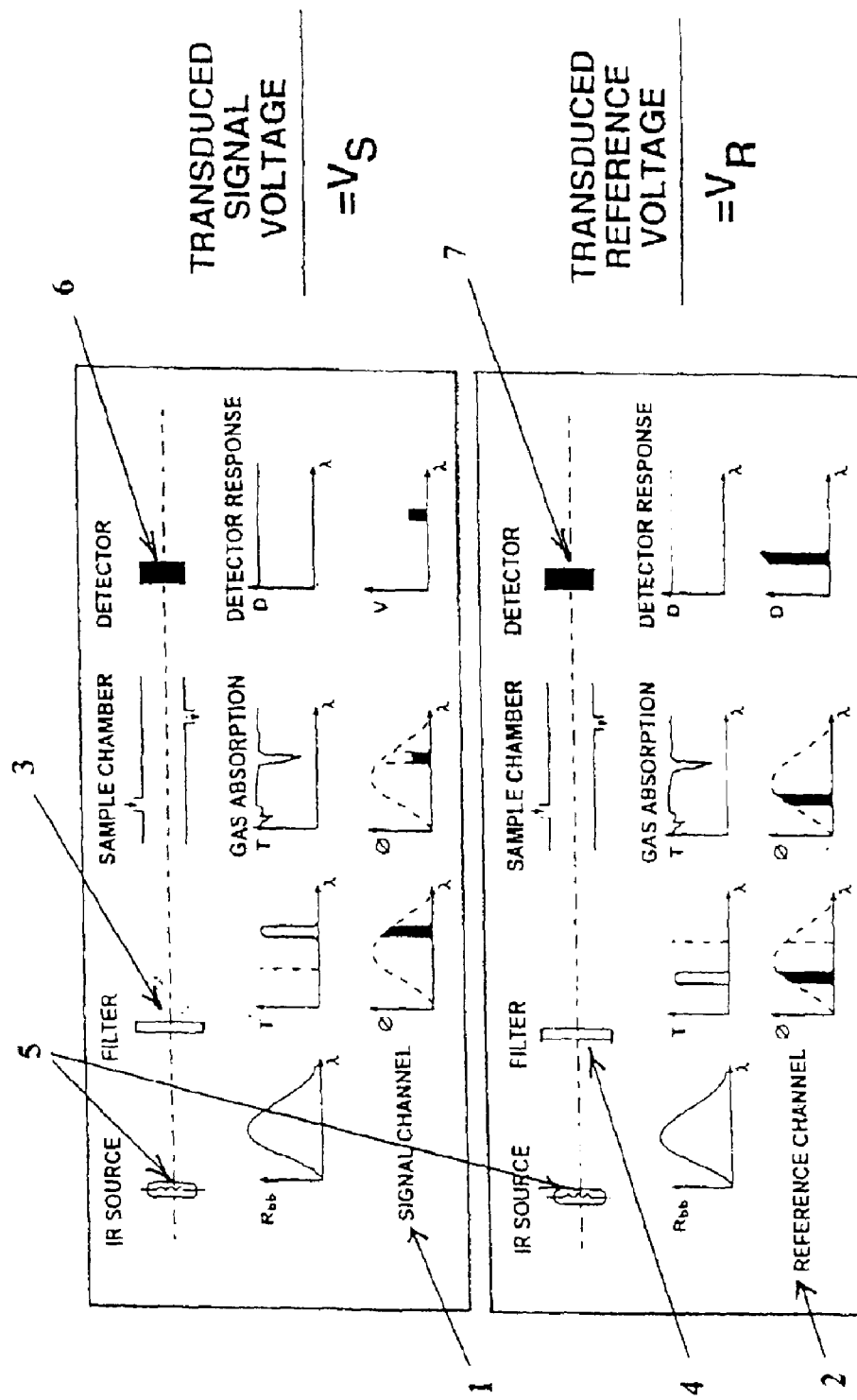
FIG. 1 depicts a Double Beam Measurement methodology.

The Non-Dispersive Infrared (NDIR) method of gas concentration measurement takes advantage of the presence of strong infrared absorption bands for many gas molecules whose atomic configurations are non-centro-symmetric. Common examples are Carbon dioxide ($CO_2$), Water Vapor ($H_2O$) and Methane ($CH_4$). Among the many NDIR gas sensing methodologies in use today, the so-called "Double Beam" technique ranks as the most widely adopted and practiced. FIG. 1 shows schematically the components and their arrangement deployed in the Double Beam methodology of NDIR gas measurement.

The reason why the name of this methodology is called "Double Beam" stems from the fact the optical arrangement for this technique comprises two optical beams or channels, one is designated as "Signal" and the other as "Reference". The so-called "Signal" beam is designed to be sensitive to the concentration of the gas to be detected in the sample chamber while the so-called "Reference" beam is designed to be substantially not. The output of the sensor is processed as the ratio of the "Signal" beam signal voltage over the "Reference" beam signal voltage. Such a processed output for the sensor serves to cancel out a number of common-mode optical disruptions or attenuations occurring in the two beams such as window obscurations by dirt so as to maintain substantially the output stability for the sensor over time.

As shown in FIG. 1, two beams labeled respectively as the Signal channel 1 and the Reference channel 2 are intentionally set up for this method to work. The setting up of these two channels or beams is achieved via the judicial choice of two narrow spectral band-pass filters 3 and 4 for the Signal and the Reference channels respectively. The spectral filter 3 defines a narrow spectral pass-band coincident with the chosen absorption band of the gas to be detected while the spectral filter 4 defines a narrow spectral pass-band that is free of any absorption bands of the gas. The signal voltages for each of the two channels 1 and 2 are generated from a single infrared source 5 and respectively with separate detectors 6 and 7 as depicted in FIG. 1. The Double Beam measurement method processes the ratio $R=V_S/V_R$ where $V_S$ is the voltage signal for the Signal channel 1 and $V_R$ is the voltage signal for the Reference channel 2 respectively. To complete the gas measurement capability for the sensor, the ratio R is calibrated against known concentrations of the gas to be detected present in the sample chamber. Once properly calibrated, such a "Double-Beam" NDIR gas sensor can be used to measure the concentration of the gas to be detected that is present in the sample chamber.

By processing the ratio R of the voltage signals of the respective Signal and Reference beams, any common-mode changes in the sensor which affect equally the Signal and the Reference beams are cancelled and these changes therefore are not reflected in the processed signal $R=V_S/V_R$ and the output of the sensor remains stable or drift-free. However, if the change over time, short-term or long-term, of one or more components of the sensor affects the Signal and the Reference channel differently, then the processed signal $R=V_S/V_R$ will change resulting in the undesirable drifts for the sensor output over time.

For example, if only the output radiation level of the common infrared source 5 (see FIG. 1) changes but not its spectral content, such changes will in effect be cancelled by processing the signal of $R=V_S/V_R$. Unfortunately, the radiation emitted by an infrared source, dependent upon its operational temperature, carries, in addition to a predictable radiation intensity level, a unique spectral content according to Planck's Radiation Law otherwise known as the Blackbody Curves. Consequently any change for the infrared source such as aging will always include a concomitant change in its spectral content. Such a change will affect differently the voltage signal for both the Signal channel and the Reference channel due to the different spectral positions of their respective bandpass filters, resulting in an undesirable drift for the sensor output over time.

The Double Beam measurement methodology for an NDIR gas sensor is susceptible to changes of its infrared source due to aging and to any environmental temperature changes that might affect the immediate surroundings of the source. The reason is that any such changes carry with them noticeable shifts in the spectral radiation output of the infrared source. Since each of the "Signal" and the "Reference" channels possesses its own narrow bandpass spectral filter, their reactions to these spectral content changes will therefore be different leading to unavoidable changes in the sensor output. Since the infrared source of an NDIR gas sensor will inevitably age over time, the output of an NDIR gas sensor designed with this "Double-Beam" measurement methodology cannot and will not remain stable over time.

Furthermore, its output could also be susceptible to drifts due to any short-term environmental temperature changes surrounding the sensor which could in turn affect the operating temperature of the source. In addition to the infrared source changes, this methodology is also susceptible to changes in other sensor components. Since the Signal channel 1 and the Reference channel 2 (see FIG. 1) have separate autonomous detectors and band-pass filters, if the temperature of these components does not track one another for whatever reason(s), either short-term or long-term over time, the sensor output will also change and these changes will not be eliminated by the mere processing of the ratio $R=V_S/V_R$ as its signal output. For these reasons, a better NDIR gas measurement methodology, other than the presently deployed Double Beam, is highly desirable and needed in order to improve the performances of future NDIR gas sensors.

The use of a spectrally neutral filter (i.e. no absorption by the gas to be detected) at a different wavelength from that of the gas' absorption band in order to create a Reference channel so that the ratio $R=V_S/V_R$ can be processed as the sensor's output, where $V_S$ and $V_R$ are respectively the voltages of the Signal and Reference channels (see FIG. 1), does not work as well as expected. Since the primary purpose of the Double Beam methodology is to create a Reference channel whose signal output remains substantially unchanged irrespective of the absence or presence of the gas to be detected in any concentration level in the sample chamber, this can be achieved via the currently invented technique called "Saturation Filtering". This novel concept of creating a "Saturation Filtering" Reference beam for an NDIR gas sensor similar to but different from the Double Beam measurement methodology is schematically illustrated in FIG. 2.

Figure 2:
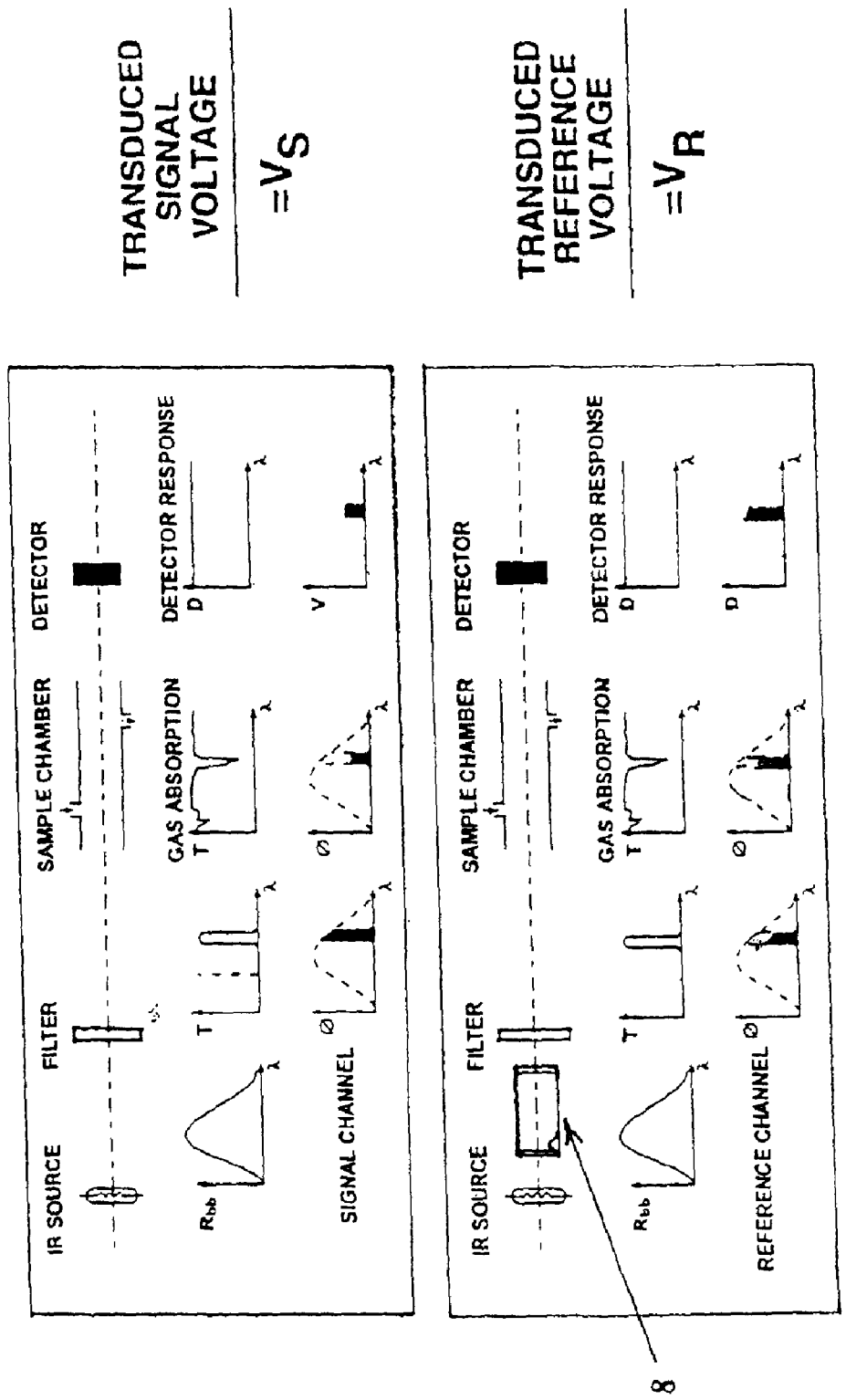
FIG. 2 depicts the Saturation Filtering Reference methodology of the present invention.

There are a couple of differences between the Double Beam configuration as depicted in FIG. 1 from that of the "Saturated Filtering" configuration shown in FIG. 2. First and utmost, the filter used for the Reference channel in the "Saturated Filtering" methodology is exactly the same as that used for the Signal channel. In other words, it is the same spectral filter that contains the absorption band of the gas to be detected used in the Signal channel (see channel 1 of FIG. 1). Second, included in the Reference beam for the Saturated Filtering" methodology is a saturation cell 8 (see FIG. 2) having a length L' cm and containing a high concentration c' of the gas to be detected expressed in atmosphere (atm) where 1 atm=100% of the gas. For attaining the best performance, the values L' and c' are designed in such a way so that the resulting absorber concentration c'L' atm-cm of cell 8 is at least an order of magnitude greater than cL atm-cm designed for the sensor, where c is the maximum concentration of the gas to be detected expressed in atm and L is the sample chamber length in cm of the sensor. Thus if the length of cell 8 is 1 cm and it is filled and sealed with 100% of the gas in question, then the absorber concentration for cell 8 will be 1 atm-cm. On the other hand, if the sensor is designed to measure up to 5,000 ppm of the gas or 0.005 atm and the sample chamber length of the sensor is 15 cm, then the absorber concentration of the sensor is 0.075 atm-cm. In this case the parameters for cell 8 would be appropriately designed for best performance as its L'c'=1 atm-cm is at least an order of magnitude greater than the Lc=0.075 atm-cm for the sensor.

When the Reference beam for the "Saturated Filtering" methodology is set up according to the way described above, the Reference signal output stays relatively constant even when the concentration of the gas inside the sample chamber of the sensor approaches its maximally designed value. This is because of the fact that radiation from the infrared source has to first pass through cell 8 before going through the sample chamber and then to the Reference detector (see FIG. 2). But since saturation cell 8 contains a very high concentration of the gas, therefore most of the radiation that is spectrally defined by the narrow band-pass filter and lies within the absorption band of the gas to be detected has already been eliminated via absorption before reaching the sample chamber and ultimately the Reference detector. Thus the Reference signal always remains about the same level irrespective of whether there is any gas to be detected inside the sample chamber for the sensor. The "Saturated Filtering" methodology has therefore effectively also created a Reference beam having a relatively non-absorbing spectral characteristic as that for the neutral band-pass filter of the conventional Double Beam method.

But there is a very significant advantage for the Saturated Filtering methodology over the Double Beam technique. Whereas the signal output of the sensor utilizing a Double Beam methodology is susceptible to any changes in the infrared source of the sensor as pointed out earlier, the signal output for the Saturated Filtering methodology remains virtually the same irrespective of the infrared source changes. This is because of the fact that the Signal beam and the Reference beam in this case are designed to have the same narrow band-pass filter and therefore have the same spectral characteristics. Thus when the signal output of the sensor is expressed as the ratio of the signals for these two channels, the ratio remains virtually constant as the beams are affected equally by the changes of the infrared source (both spectrally and intensity level-wise) and these changes are canceled against one another. Furthermore any environmental changes that affect the temperature surrounding of the source that might result in changing its operating temperature are also automatically neutralized.

For very much the same reason, NDIR gas sensors utilizing a waveguide as a sample chamber, any extraneous infrared source effects caused by the temperature changes imparted to the waveguide are completely eliminated when the Saturated Filtering technique instead of the conventional Double Beam one is implemented. Since for the Saturation Filtering methodology individual filters and detectors for the two beams have identical spectral and physical characteristics, as long as these sensor components are mounted on the same thermal platform so that their temperatures track one another, drifts due to any temperature changes are also kept very much to a minimum.

For an NDIR gas sensor implemented with the Double Beam methodology, the construct for the entire sensor including its sample chamber, source module and detector module are normally temperature regulated (typically to 35° C.) in order to control and minimize its signal output drifts on a short or long-term basis over time. For the sensor implemented with the Saturation Filtering methodology, such temperature regulation for the sensor is no longer necessary as long as the Signal and the Reference detectors with the identical built-in narrow bandpass spectral filter share a common thermal platform so that their temperatures track one another at all times. The reason is that for the entire sensor we now essentially have only one beam. Both the Signal and Reference beams have the same filters that are spectrally identical. They also have similar detectors that are manufactured in very much the same way. Finally, they share the same infrared source. Thus, if there are any changes at all, processing the ratio of the Signal channel over the Reference channel as the sensor output for the Saturation Filtering methodology can virtually eliminate all the drifts over time, either short-term or long-term, that otherwise would be there for the Double Beam measurement technique.

Figure 3:
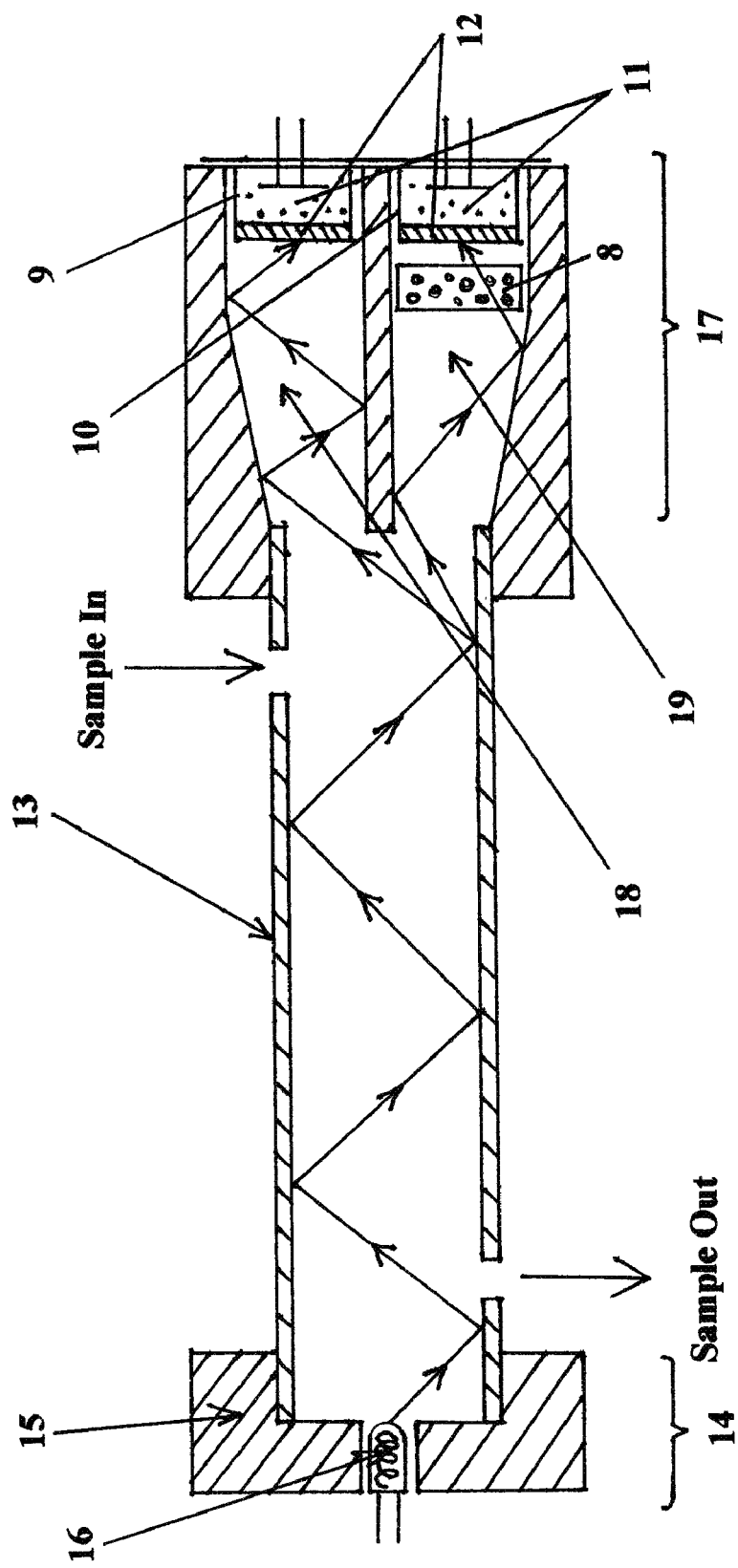
FIG. 3 depicts a preferred embodiment of an NDIR gas sensor designed in accordance with the present invention.

FIG. 3 depicts the optical component layout for a preferred embodiment of the present invention. As shown in FIG. 3, both the Signal channel detector 9 and the Reference channel detector 10 are entrapped with 100% Nitrogen 11 and have the same narrow band pass spectral filter 12 which is used to detect the gas of interest in the sample chamber 13. As an example, the filter designed to be used for the detection of $CO_2$ gas could have a Center Wavelength (CWT)=4.26μ and a Full Width Half Maximum (FWHM)=0.14μ. In the current preferred embodiment of an NDIR gas sensor in accordance with the present invention, both detectors 9 and 10 are thermally connected to the sensor sample chamber 13 which is in essence an aluminum waveguide sample chamber. Consequently detectors 9 and 10 always share the same thermal platform with each other. One end 14 of the sensor sample chamber 13 is the source mount 15 housing the common infrared source 16. The other end 17 of the sensor sample chamber 13 is partitioned out respectively into the Signal channel portion 18 and the Reference channel portion 19. The Signal channel detector 9 is located at the end of the signal channel portion 18. The Reference channel detector 10 is located at the end of the Reference channel portion 19 after the saturation cell 8 (see FIG. 2). Because of the fact that detectors 9 and 10 share the same common thermal platform, no significant temperature difference could exist at any time between the two detectors that would alter in any way their respective responsivities. Thus the ratio of the Signal channel voltage output over the Reference channel voltage output will virtually be independent of the ambient temperature of the environment wherein the sensor is located.

Figure 4:
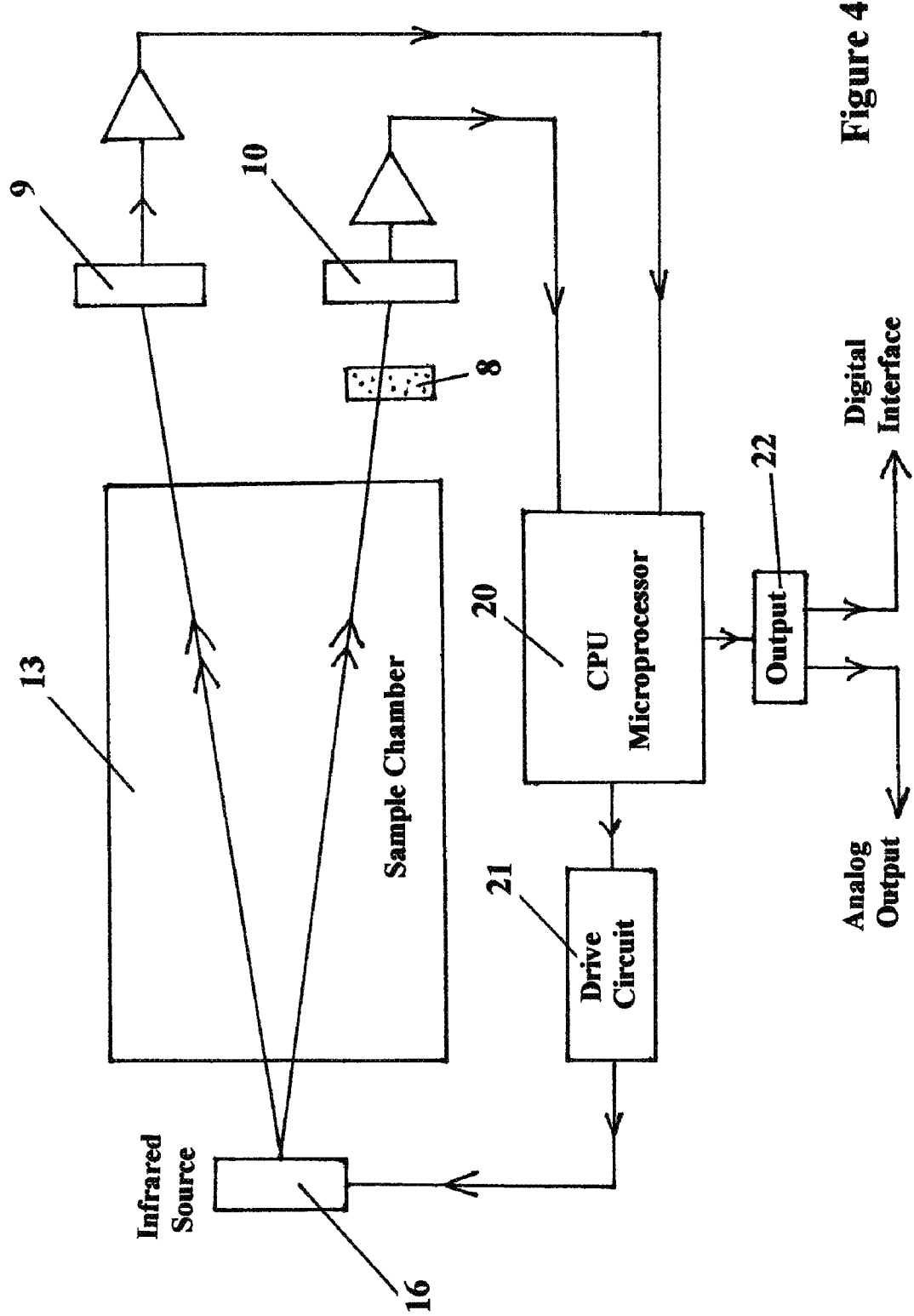
FIG. 4 depicts schematically a simplified electronic signal processing circuit for the implementation of an NDIR gas sensor in accordance with a preferred embodiment of the present invention.

FIG. 4 depicts a simplified electronic signal processing circuit for the implementation of a preferred embodiment of the present invention. With reference to FIG. 4, the entire electronic signal processing circuit is built around a microprocessor or Central Processing Unit (CPU) 20 with its associated software (not shown in FIG. 4). The CPU 20 engineers a voltage pulsing circuit 21 to drive the infrared source 16 (see FIG. 3) for the NDIR gas sensor. Signals generated by the Signal channel detector 9 and the Reference channel 10 (see FIG. 3) after the radiation emanating from the infrared source 16 traverses the sample chamber 13 are routed to the CPU 20 for processing. Sampling signals are provided by the software of the CPU 20 for the synchronized processing of signals generated by the Signal and Reference channel detectors with the infrared source. Finally, the software for the CPU 20 also generates the NDIR gas sensor outputs 22 in both analog and digital formats.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. Apparatus for detecting a gas of interest utilizing a non-dispersive infrared sensor, the apparatus comprising:
   an infrared source;
   a signal channel with a signal detector;
   a reference channel with a reference detector and a saturation cell containing the gas of interest; and
   a single narrow band-pass spectral filter used for both the signal channel and the a reference channel;
   wherein both the signal detector and the reference detector are mounted on a single thermal platform;
   wherein a reference channel signal remains substantially unchanged irrespective of the absence or presence of the gas to be detected in any concentration level in the sample chamber; and
   wherein the signal detector produces a signal output, the reference detector produces a reference output, and the ratio of the signal output over the reference output remains substantially the same irrespective of changes in the infrared source.

2. The apparatus of claim 1 wherein the saturation cell contains substantially 100% of the gas of interest.

3. The apparatus of claim 1 wherein the saturation cell has a length L' and contains a concentration c' of the gas of interest such that a resulting saturation cell concentration of the gas of interest of (L')×(c') is at least an order of magnitude greater than a sample cell concentration of the gas of interest of (L)×(c) where L is a length of a sample cell of the signal channel and c is a maximum concentration of the gas of interest in the sample cell.

4. The apparatus of claim 1 wherein the reference detector and the signal detector are mounted in a single structure of a heat transmitting material.

5. The apparatus of claim 4 wherein the heat transmitting material is comprised of aluminum.

6. A non-dispersive infrared sensor, comprising:
   a sample chamber through which a gas of interest flows;
   an infrared source;
   a spectral filter;
   a reference detector for detecting a reference channel signal;
   a saturation cell containing substantially 100% of the gas of interest;
   a signal detector for detecting a signal channel signal; and
   electronics for processing a ratio of the signal channel signal to the reference channel signal;
   wherein the spectral filter has a narrow spectral pass-band coincident with a chosen absorption band of the gas of interest;
   wherein the infrared source, the spectral filter, the saturation cell, the sample chamber and the reference detector form a reference channel;
   wherein the infrared source, the spectral filter, the sample chamber and the signal detector form a signal channel;
   wherein the reference detector and the signal detector are mounted on a single thermal platform so that their temperatures track one another; and
   wherein the reference channel signal remains substantially unchanged irrespective of the absence or presence of the gas to be detected in any concentration level in the sample chamber.

7. The non-dispersive infrared sensor of claim 6 wherein a ratio of the signal channel signal over the reference channel signal remains substantially the same irrespective of changes in the infrared source.

8. The non-dispersive infrared sensor of claim 7 wherein the saturation cell has a length L' and contains a concentration c' of the gas of interest such that a resulting saturation cell concentration of the gas of interest of (L')×(c') is at least an order of magnitude greater than a sample cell concentration of the gas of interest of (L)×(c) where L is a length of the sample cell and c is a maximum concentration of the gas of interest in the sample cell.

9. The non-dispersive infrared sensor of claim 7 wherein the gas of interest is water vapor and the chosen absorption band is a strong absorption band of water vapor.

10. The non-dispersive infrared sensor of claim 7 wherein the gas of interest is a hydrocarbon.

11. The non-dispersive infrared sensor of claim 7 wherein the gas of interest is carbon dioxide and the chosen absorption band is a strong absorption band of carbon dioxide.

12. The non-dispersive infrared sensor of claim 7 wherein the reference detector and the signal detector are mounted in a single structure of a heat transmitting material.

13. The non-dispersive infrared sensor of claim 7 wherein the single thermal platform is an aluminum structure.

14. A method comprising utilizing a single narrow band-pass spectral filter in a non-dispersive infrared sensor for both a signal channel and a reference channel used to detect a gas of interest through use of a ratio of a signal output detected by a signal detector in the signal channel over a reference output detected by a reference detector in the reference channel which remains substantially the same irrespective of changes in an infrared source used in the non-dispersive infrared sensor, wherein the reference channel also contains a saturation cell containing the gas of interest and both the signal detector and the reference detector are mounted on a single thermal platform.

15. The method of claim 14 wherein a reference channel signal remains substantially unchanged irrespective of the absence or presence of the gas to be detected in any concentration level in a sample chamber of the non-dispersive infrared sensor.

16. The method of claim 14 wherein the saturation cell has a length L' and contains a concentration c' of the gas of interest such that a resulting saturation cell concentration of the gas of interest of (L')×(c') is at least an order of magnitude greater than a sample cell concentration of the gas of interest of (L)×(c) where L is a length of a sample cell of the signal channel and c is a maximum concentration of the gas of interest in the in the sample cell.

17. The method of claim 14 wherein the saturation cell contains substantially 100% of the gas of interest.

* * * * *